(12) United States Patent
Snedeker et al.

(10) Patent No.: US 12,064,335 B2
(45) Date of Patent: Aug. 20, 2024

(54) LOOP/ BUTTON SYSTEM FOR TENDON AND LIGAMENT RECONSTRUCTION

(71) Applicant: ZURIMED TECHNOLOGIES AG, Zurich (CH)

(72) Inventors: Jess Snedeker, Zurich (CH); Xiang Li, Zumikon (CH); Elias Bachmann, Meilen (CH); George Rosenberg, Zurich (CH)

(73) Assignee: ZURIMED TECHNOLOGIES AG, Zurich (CH)

( * ) Notice: Subject to any disclaimer, the term of this patent is extended or adjusted under 35 U.S.C. 154(b) by 149 days.

(21) Appl. No.: 16/305,899

(22) PCT Filed: May 31, 2016

(86) PCT No.: PCT/EP2016/062257
§ 371 (c)(1),
(2) Date: Nov. 30, 2018

(87) PCT Pub. No.: WO2017/207027
PCT Pub. Date: Dec. 7, 2017

(65) Prior Publication Data
US 2020/0315774 A1   Oct. 8, 2020

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0404* (2013.01);
(Continued)

(58) Field of Classification Search
CPC .... A61B 2017/0414; A61B 2017/0459; A61B 2017/0456; A61B 2017/0458;
(Continued)

(56) References Cited

U.S. PATENT DOCUMENTS

| 6,767,037 | B2 | 7/2004 | Wenstrom |
| 2003/0130694 | A1* | 7/2003 | Bojarski ............... A61F 2/0805 606/228 |

(Continued)

FOREIGN PATENT DOCUMENTS

WO   2012154922   11/2012

*Primary Examiner* — Mohamed G Gabr
(74) *Attorney, Agent, or Firm* — JMB Davis Ben-David

(57) ABSTRACT

The invention relates to a medical implant (1), comprising at least a first cortical fixation device (200) for fixing a ligament or tendon graft (G) in a desired position, wherein said first cortical fixation device (200) comprises a body (201) having a front side (201*a*) and a rear side (201*b*), which rear side (201*b*) faces away from the front side (201*a*), and wherein said body (201) comprises a first and an adjacent second through-hole (210, 211), which through-holes (210, 211) extend from the front side (201*a*) to the rear side (201*b*) of said body. According to the invention the medical implant (1) further comprises a first suture thread (100) extending through the through-holes (210, 211) and forming a twisted loop (104) and a non-twisted loop (105) on the front side (201*a*) of the body (201), and a sliding knot (108) on the rear side (201*b*) of the body (201), and wherein the medical implant (1) comprises a second suture thread (300) extending through the sliding knot (108).

27 Claims, 7 Drawing Sheets

Figure 1:
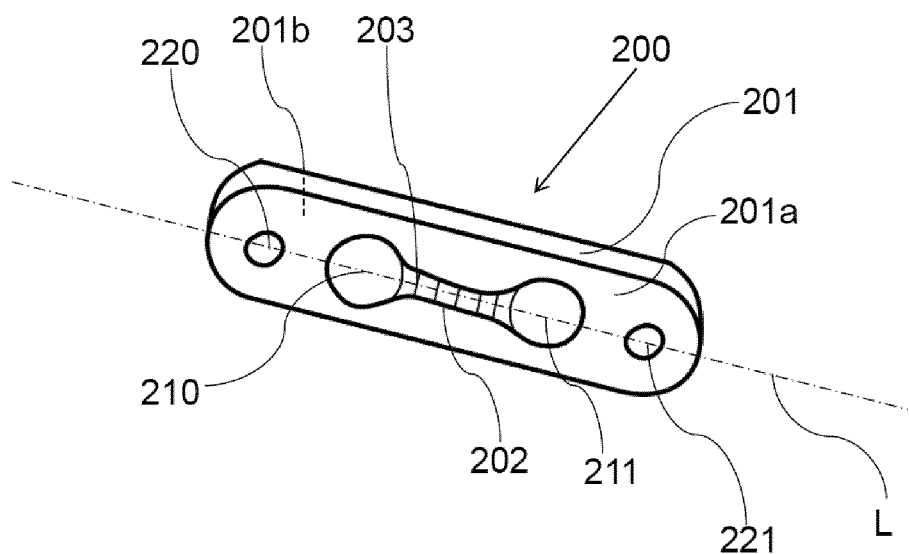

(52) U.S. Cl.
CPC ............... *A61B 2017/0456* (2013.01); *A61B 2017/0458* (2013.01); *A61B 2017/0459* (2013.01); *A61B 2017/0464* (2013.01); *A61F 2002/0852* (2013.01); *A61F 2002/0882* (2013.01)

(58) Field of Classification Search
CPC .... A61B 2017/0404; A61B 2017/0464; A61B 2017/0475
See application file for complete search history.

(56) References Cited

U.S. PATENT DOCUMENTS

| | | |
|---|---|---|
| 2010/0114161 A1 | 5/2010 | Bojarski et al. |
| 2010/0324676 A1 | 12/2010 | Albertorio et al. |
| 2012/0059417 A1* | 3/2012 | Norton ............... A61B 17/1655 606/232 |
| 2012/0180291 A1* | 7/2012 | Oren ................... A61B 17/0401 29/428 |
| 2013/0096612 A1 | 4/2013 | Zajac et al. |
| 2014/0074239 A1 | 3/2014 | Albertorio et al. |
| 2016/0157851 A1* | 6/2016 | Spenciner ............ A61F 2/0811 606/232 |

* cited by examiner

LOOP/ BUTTON SYSTEM FOR TENDON AND LIGAMENT RECONSTRUCTION

Cross-Reference to Related Application

This is the U.S. National Stage of International Application No PCT/EP2016/062257 filed on May 31, 2016, which was published in English under PCT Article 21(2).

The invention relates to a medical implant, particularly for the reconstruction of the anterior cruciate ligament (ACL).

Due to its anatomical location, the ACL is subjected to potentially extreme forces during sports and other physical activities. Rupture of the ACL has been counted as the most frequent and severe of ligament injuries.

For ACL reconstruction cortical fixation devices (CFD) are often used. Such a cortical fixation device is small fixation device that helps to secure the tendon or ligament graft to its desired position when performing the anterior cruciate ligament (ACL) reconstruction. Such CFDs may also be used in conjunction with other ligament or tendon grafts or other flexible (e.g. elongated) members.

The shape of known titanium-made CFDs usually resembles that of an elongated, narrow button. Often, CFDs are therefore colloquially referred to as 'buttons'.

In ACL reconstruction, fixation of the graft (e.g. hamstring graft or patellar bone-tendon-bone graft (BTB)) onto the cortex of the femur at the proximal end of the femoral tunnel is a crucial part of a successful procedure.

Here, titanium (or steel)-made CFDs hold a continuous loop or sutures on their bottom side, usually made out of polyester or similar material. This loop is the attachment site of the (e.g. hamstring or BTB) graft. Once the graft is attached, the CFD can be pulled through the tibial or femoral tunnel by temporarily attached sutures until it reaches the cortex of the femur. By either pulling back on the graft or using a second suture to flip the CFD, the CFD is pulled flush against the cortex of the femoral bone. The graft can be seen as being suspended from the cortex of the femur.

Variations between devices are present in current state-of-the-art products which differ mainly regarding adjustment for different trans-osseous overall tunnel lengths of the posterolateral or anteromedial tunnels, respectively. When using either of the two tunnels, the overall tunnel length is comprised of channel depth and socket depth. Such a transfemoral tunnel is drilled through proximally from the distal end of the femur. A socket is reamed over the channel in which the graft will later be incorporated into the femoral bone. Socket depth and the resulting overall tunnel lengths vary individually and are highly dependent on the surgeons and graft choice. CFDs need to account for these varying lengths; therefore two main types of CFDs have emerged on the market: Adjustable-length CFDs and fixed-length CFDs.

Adjustable-length CFDs allow for a length adjustment of the suture loop that is attached to the graft. With such a CFD, a surgeon can drill the trans-osseous tunnel to his or her discretion and fit the CFD according to the drilled lengths.

The size of CFDs determines the diameter of the trans-osseous tunnel needed to be drilled. In combination with the socket depth, these two parameters are possible causes for tunnel widening or even breaching of the lateral femoral wall. CFDs that are too big or require a longer socket depth due to having short continuous loops may increase the risk of clinical failure.

While it has been well established that the ultimate strength of CFDs is very high and not highly relevant for clinical failure, the weak link of CFDs is the possibility of loop lengthening. It has been described in various cadaver models that the graft-holding loops of adjustable-length CFDs can stretch under high cyclic loading. It is considered as a clinical failure if the stretched displacement is longer than 3 mm.

Based on the above, the problem underlying the present invention is to provide a medical implant that can be positioned in an easy manner and particularly prevents said stretching.

This problem is solved by a medical implant having the features of claim 1. Preferred embodiments are stated in the sub claims and are described below.

According to claim 1, a medical implant is disclosed, comprising at least a first cortical fixation device for fixing a ligament or tendon graft (or some other flexible member) in a desired position, particularly in case of an anterior cruciate ligament (ACL) reconstruction, wherein said first cortical fixation device comprises a body having a front side and a rear side, which rear side faces away from the front side, and wherein said body comprises a first and an adjacent second through-hole, which through-holes extend from the front side to the rear side of said body. According to the invention the medical implant further comprises a first suture thread extending through said through-holes and forming a twisted loop and a non-twisted loop on the first side of the body, and a sliding knot on the rear side of the body, and wherein the medical implant comprises a second suture thread extending through the sliding knot.

In this way the invention advantageously provides an adjustable, self-tightening knot that can slide on the first suture thread. This allows the surgeon to adjust (e.g. shorten) the (twisted and non-twisted) loop length and eliminates the need to tie the knot itself in the meantime. The second suture allows the surgeon to adjust (loosen) the loop in case the loop is over-shortened.

Particularly, the sliding knot is configured to slide in a direction pointing towards the rear side of the cortical fixation device for tightening said twisted loop and said non-twisted loop against motion in the reverse direction, wherein optionally the second suture thread is configured to bring the sliding knot away from the cortical fixation device so as to loosen the twisted and the non-twisted loop and permit motion in the reverse direction.

According to a preferred embodiment of the present invention, the first suture thread comprises a first and a second free end, wherein the free ends are threaded through the two through-holes such that the suture thread forms said twisted loop and said non-twisted loop on the front side of the body.

Further, according to a preferred embodiment, the first suture thread comprises a turning loop on the rear side of the body, wherein the turning loop is formed into a Lark's head on the rear side which comprises two adjacent loops through which said free ends of the first suture thread are pulled so that said sliding knot is formed on the rear side of the body.

Further, according to an embodiment, the second suture thread extends through the two adjacent loops of the Lark's head such that the second suture thread forms a loop that can be used to adjust the sliding knot to loosen the twisted and non-twisted loop.

Further, according to an embodiment, the front side of said body comprises a slot for clamping the first suture thread, which slot extends from the first through-hole to the second through-hole. According to an alternative embodiment, the front side comprises a recess, wherein an insert is arranged in the recess, which insert forms a slot for receiving the first suture thread, which slot in turn extends from the first through-hole to the second through-hole of the body of the first cortical fixation device.

Further, according to a preferred embodiment, the slot comprises a structure for enhancing friction which can be formed in an embodiment by a plurality of teeth for securing the first suture thread. Particularly, said teeth may be integrally formed with the insert or said body of the first cortical fixation device. Advantageously, the slot allows a knot-free fixation of the first suture thread to the body of the cortical fixation device.

Furthermore, according to an embodiment, the first free end of the first suture thread is passed through the first through-hole of the body of the first cortical fixation device, so that the first suture thread comprises a first loop on the rear side of said body, and wherein the second free end of the first suture thread is passed through the second through-hole so that the first suture thread comprises a second loop on the rear side of the body.

Further, according to an embodiment, said first free end of the first suture thread is further passed through the second through-hole of the body of the first cortical fixation device so that a first portion of the first suture thread is arranged in said slot (particularly on top of said teeth), wherein said second free end of the first suture thread is further passed through said first through-hole so that a second portion of the first suture thread is arranged in said slot (particularly on top of said teeth) so that the two portions extend along each other in opposite directions. Particularly, these two portions of the first suture thread are embedded, particularly with a press-fit, within the slot comprising said friction enhancing structure (e.g. teeth). The two portions of the first suture thread tend to slide in opposite directions in case of loosening. The opposite sliding tendency and press-fit embedding into the slot comprising said structure (e.g. teeth) creates a substantial friction against loosening and elongation of said twisted and non-twisted loop. Furthermore, according to an embodiment, for shortening a length of the twisted loop as well as a length of the non-twisted loop, the first and the second loop each comprise a section extending from said sliding knot, such that, when these sections are pulled (e.g. axially) away from the rear side of the body of the first cortical fixation device, said lengths decrease.

Further, according to an embodiment, for increasing the lengths of the twisted loop and the non-twisted loop, the free ends of the second suture thread are configured to be pulled away from the rear side of the body of the first cortical fixation device such that the sliding knot is moved away from said rear side.

With this feature, the surgeon can loosen the knot after it has already been tightened. This in turn, allows for the lengthening of the graft-holding (twisted and non-twisted) loop, even after it has been tightened. A surgeon can therefore more easily re-adjust/restore the (twisted and non-twisted) loop length in case an over-pull situation happens.

Further, according to an embodiment, for securing the twisted and non-twisted loop, the free ends of the first suture thread are configured to be pulled away from the rear side of the body of the first cortical fixation device (e.g. in the axial direction of a femoral tunnel) such that the first and the second loop of the first suture thread on the rear side of said body are tightened while the twisted and the non-twisted loop of the first suture thread on the first side of said body are secured due to said parallel portions of the first suture thread being arranged in said slot, where they are preferably held by means of friction forces.

This feature advantageously eliminates the need for the surgeon to tie additional knots to secure the fixation function. "Knot-Free" means the surgeon does not have to make the knot, but only has to pull to secure the fixation. Here, pulling straight in the axial direction of the drilled tunnel is way easier for the surgeon than pulling laterally or in other directions.

Further, according to an embodiment, the body of the first cortical fixation device is formed as an elongated (e.g. flat) plate that extends along a longitudinal axis, wherein said through-holes are preferably arranged side by side in the direction of said longitudinal axis, particularly in a centered fashion.

Furthermore, according to an embodiment, the insert forming said slot and structure (e.g. teeth) is formed out of a synthetic material. This material can be selected from the group of biocompatible polymers such as polyether ether ketone (PEEK), polyethylene(PE), ultra-high-molecular-weight polyethylene (UHMWPE), poly(propylene)(PP), poly(tetrafluoroethylene) (PTFE, Teflon), poly(methyl methacrylate), ethylene-co-vinylacetate, poly(ether urethane) (PU), poly(ethylene terephthalate) (PET), etc.

Further, according to an embodiment, the two through-holes of the body of the first cortical fixation device are preferably inner through holes, i.e., said body preferably comprises two outer through-holes, wherein each outer through-hole also extends from the front side to the rear side of said body. Further, particularly, said outer through-holes face each other in the direction of the longitudinal axis, wherein the two inner through-holes are preferably arranged between the two outer through-holes. The outer through-holes may be used to handle the first CFD, e.g., by threading a suitable suture thread through the respective outer through-hole.

Furthermore, according to an embodiment, inner diameter of the inner through-holes is larger than the inner diameter of the outer through-holes.

Further, according to an embodiment, the body of the first CFD is formed out of a metal. Particularly, said metal is selected from the group comprising titanium alloy, stainless steel, cobalt-chrome alloy, nickel-titanium alloy, etc. Further, the body can also be formed out of a (e.g. high strength) biocompatible polymer, such as polyether ether ketone (PEEK), ultra-high-molecular-weight polyethylene (UHMWPE), poly(tetrafluroethylene) (Teflon), etc.

Further, the body may comprise a metal and a synthetic material or may be formed out of such a material combination.

Particularly, said inner and outer through-holes extend from the front side to the rear side of the body of the first cortical fixation device perpendicular to the longitudinal axis of said body, wherein particularly all inner and outer through holes are arranged on the longitudinal axis in a centered fashion.

According to a preferred embodiment of the present invention, the twisted loop and the non-twisted loop are connected to a tendon or ligament graft (or some other flexible member) that shall replace a defect ligament or tendon, wherein said graft extends through said twisted and non-twisted loop for fastening it to said twisted and non-twisted loop.

According to yet a further preferred embodiment of the present invention, the medical implant comprises a second cortical fixation device (CFD) for fixing said ligament or tendon graft (or another flexible member) in a desired position (particularly in case of an anterior cruciate ligament (ACL) reconstruction), wherein said second cortical fixation device comprises a body having a front side and a rear side, which rear side faces away from the front side, and wherein said body comprises a first and an adjacent second through-hole, which through-holes extend from the front side to the rear side of the body of the second CFD, and wherein the medical implant further comprises a third suture thread forming a twisted twisted loop and an non-twisted loop on the first side of the body of the second CFD, and a sliding knot on the rear side of the body of the second CFD, and wherein the medical implant comprises a fourth suture thread extending through said sliding knot on the rear side of the body of the second CFD, Further, according to an embodiment, the sliding knot on the second CFD is also a self-tightening sliding knot that is configured to slide in a direction pointing towards the rear side of the second CFD, wherein this sliding knot is configured to be loosened by means of the fourth suture thread (see also discussion of said motion above).

Further, according to an embodiment, the third suture thread comprises a first and a second free end, wherein these free ends are threaded through the two through-holes of the second CFD such that the third suture thread forms said twisted loop and said non-twisted loop on the front side of the body of the second CFD.

Further, according to an embodiment, the third suture thread comprises a turning loop on the rear side of the body of the second CFD, wherein the turning loop is formed into a Lark's head which comprises two adjacent loops through which said free ends of the third suture thread are pulled so that said sliding knot is formed on the rear side of the body of the second CFD.

Further, according to an embodiment, the fourth suture thread extends through the two adjacent loops of the Lark's head such that the fourth suture thread forms a loop.

Particularly, the first side of the body of the second cortical fixation device comprises a slot for receiving the third suture thread, which slot extends from the first through-hole to the second through-hole of the body of the second cortical fixation device. Alternatively, as before, the first side of said body may comprises a recess, wherein an insert is arranged in this recess, which insert forms a slot for receiving the third suture thread. Particularly, this slot extends from the first through-hole to the second through-hole of body of the second cortical fixation device.

Further, according to an embodiment, the slot of the second cortical fixation device comprises a structure for enhancing friction, particularly a plurality of teeth, for securing the third suture thread. Also here, said teeth may be integrally formed with the insert or said body of the second cortical fixation device.

Further, according to an embodiment, the first free end of the third suture thread is passed through the first through-hole of the second cortical fixation device so that the third suture thread comprises a first loop on the rear side of the body of the second cortical fixation device, and wherein the second free end of the third suture thread is passed through the second through-hole of the second cortical fixation device so that the third suture thread comprises a second loop on the rear side of the body of the second cortical fixation device.

Further, according to an embodiment, said first free end of the third suture thread is further passed through the second through-hole of the body of the second cortical fixation device so that a first portion of the third suture thread is arranged in said slot of the second cortical fixation device (particularly on top of said teeth), wherein said second free end of the third suture thread is further passed through said first through-hole of the body of the second cortical fixation device so that a second portion of the third suture thread is arranged in said slot (particularly on top of said teeth) so that the two portions extend along each other in opposite directions.

Particularly, for shortening a length of the twisted loop as well as a length of the non-twisted loop of the third suture thread, the first and the second loop of the third suture thread each comprise a section extending from said sliding knot of the third suture thread, such that, when these sections are pulled away from the rear side of the body of the second cortical fixation device, said lengths decrease.

Further, particularly, for increasing the lengths of the twisted and the non-twisted loop, the free ends of the fourth suture thread are configured to be pulled away from the rear side of the body of the second cortical fixation device such that the sliding knot of the third suture thread is moved away from the rear side.

Further, particularly, for securing the twisted and non-twisted loop of the third suture thread, the free ends of the third suture thread are configured to be pulled away from the rear side (e.g. in the axial direction of a femoral tunnel) of the body of the second cortical fixation device such that the first and the second loop on the rear side are tightened while the twisted and the non-twisted loop of the second cortical fixation device are secured due to said portions of the third suture thread being arranged in said slot of the second cortical fixation device.

Further, the second cortical fixation device can be designed like the first cortical fixation device, i.e., its body may be formed as an elongated plate that extends along a longitudinal axis, wherein said through-holes are arranged side by side in the direction of said longitudinal axis.

Further, its insert may be formed out of a synthetic material.

Further, also here, the two through-holes of the body of the second cortical fixation device are inner through holes, wherein said body comprises two outer through-holes, wherein each outer through-hole extends from the front side to the rear side of the body of the second cortical fixation device, and wherein said outer through-holes face each other in the direction of the longitudinal axis, wherein the two inner through-holes are arranged between the two outer through-holes.

Further, the inner diameter of the inner through-holes of the second cortical fixation device can be larger than the inner diameter of the outer through-holes.

Further, the body of the second cortical fixation device may be formed out of a metal, too.

Further, the inner and the outer through-holes of the second cortical fixation device particularly extend from the front side to the rear side of the body of the second cortical fixation device perpendicular to the longitudinal axis, wherein all inner and outer through holes are arranged on the longitudinal axis in a centered fashion.

According to yet a further aspect of the present invention, a cortical fixation device for fixing a ligament or tendon graft in a desired position is disclosed, comprising a body having a front side and a rear side, which rear side faces away from the front side, and wherein said body comprises a first and an adjacent second through-hole, which through-holes extend from the front side to the rear side of said body.

Further, according to an embodiment, the front side of the body comprises a slot for receiving a suture thread for providing a knot-free fixation of the suture thread to the body, which slot extends from the first through-hole to the second through-hole.

Further, according to an embodiment, the front side comprises a recess, wherein an insert is arranged in the recess, which insert forms said slot for receiving said suture thread.

Further, according to an embodiment, the slot comprises a structure for enhancing friction, e.g. in the form of a plurality of teeth, for securing said suture thread.

Further, according to an embodiment, the body is formed as an elongated plate that extends along a longitudinal axis, wherein said through-holes are arranged side by side in the direction of said longitudinal axis.

Further, according to an embodiment, the insert is formed out of a synthetic material (e.g. one of the synthetic materials described herein).

Further, according to an embodiment, the two through-holes are inner through holes, wherein said body comprises two outer through-holes, wherein each outer through-hole extends from the front side to the rear side, and wherein said outer through-holes face each other in the direction of the longitudinal axis, wherein the two inner through-holes are arranged between the two outer through-holes.

Further, according to an embodiment, the inner diameter of the inner through-holes is larger than the inner diameter of the outer through-holes.

Further, according to an embodiment, the body is formed out of a metal (e.g. one of the metals described herein).

According to yet another aspect of the present invention, a method for fixing a ligament or tendon graft (or some other e.g. elongated flexible member) in a desired position is disclosed, wherein the method particularly uses a medical implant according to the invention, wherein a first cortical fixation device is provided that comprises a body having a front side for butting against a bone to which the ligament or tendon graft is to be fixed, a rear side, which rear side faces away from the front side, and a slot on the front side optionally comprising a structure for enhancing friction (e.g. a plurality of teeth), and wherein said body comprises a first and an adjacent second through-hole, which through-holes extend from the front side to the rear side of said body, wherein a first suture thread is threaded through said through-holes, and formed into a twisted loop and a non-twisted loop being arranged on the first side of the body, wherein said twisted and said non-twisted loop are looped around a section of said ligament or tendon graft to hold the latter and fix it to said bone, and wherein the first suture thread is tied to form a sliding knot on the rear side of the body, and wherein a second suture thread is threaded through said sliding knot to allow loosening of the sliding knot, and wherein two portions of said first suture thread are clamped within the said slot for providing a knot-free fixation of the first suture thread in said slot.

The method according to the invention can be further specified using the features of the implant according to the invention described herein.

Particularly, in case of ACL reconstruction the front side of the body of the first CFD is arranged such that it butts against the tibia or femur, wherein the twisted and the non-twisted loop extend through a bore hole drilled into the tibia or femur. In case a second CFD is used, its front side is arranged such that it butts against the other bone (i.e. femur or tibia) and the twisted and non-twisted loop attached to the second CFD then extend through a bore hole in the other bone (i.e. femur or tibia) so that the ligament graft that is fixed on both sides to a twisted and a non-twisted loop and can extend between the two CFDs, i.e., between the tibia and femur.

Figure 2:
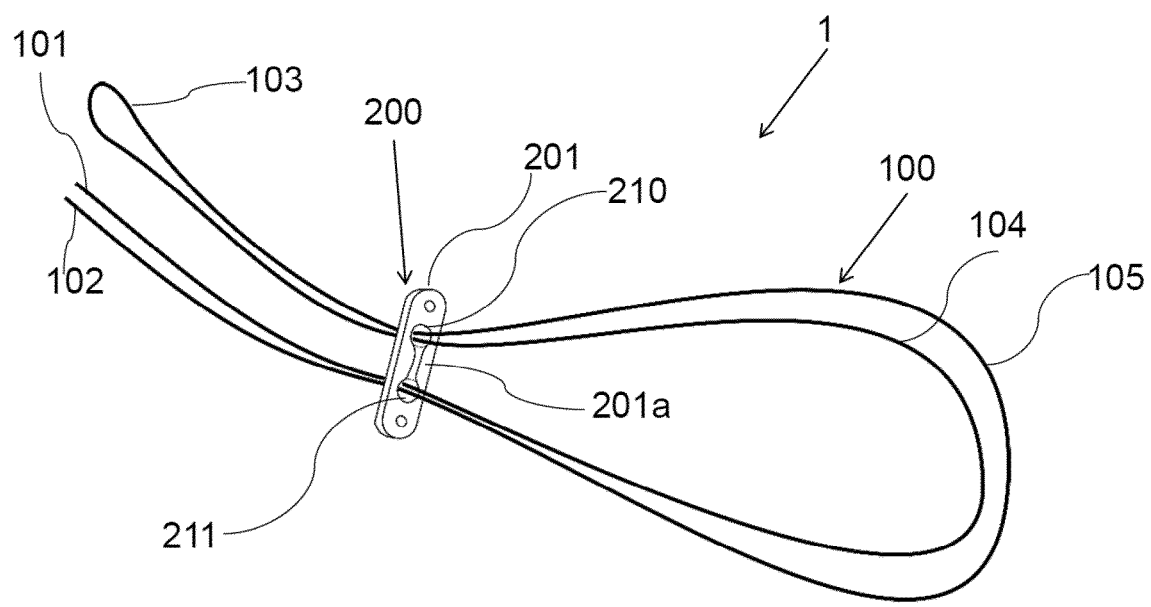
Figure 3:
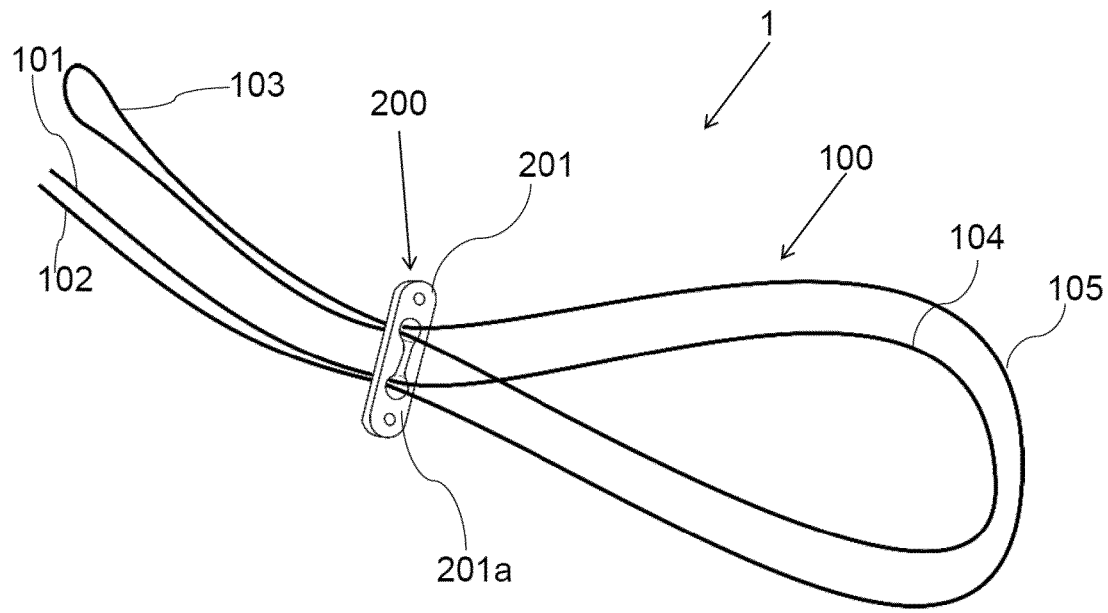
Figure 4:
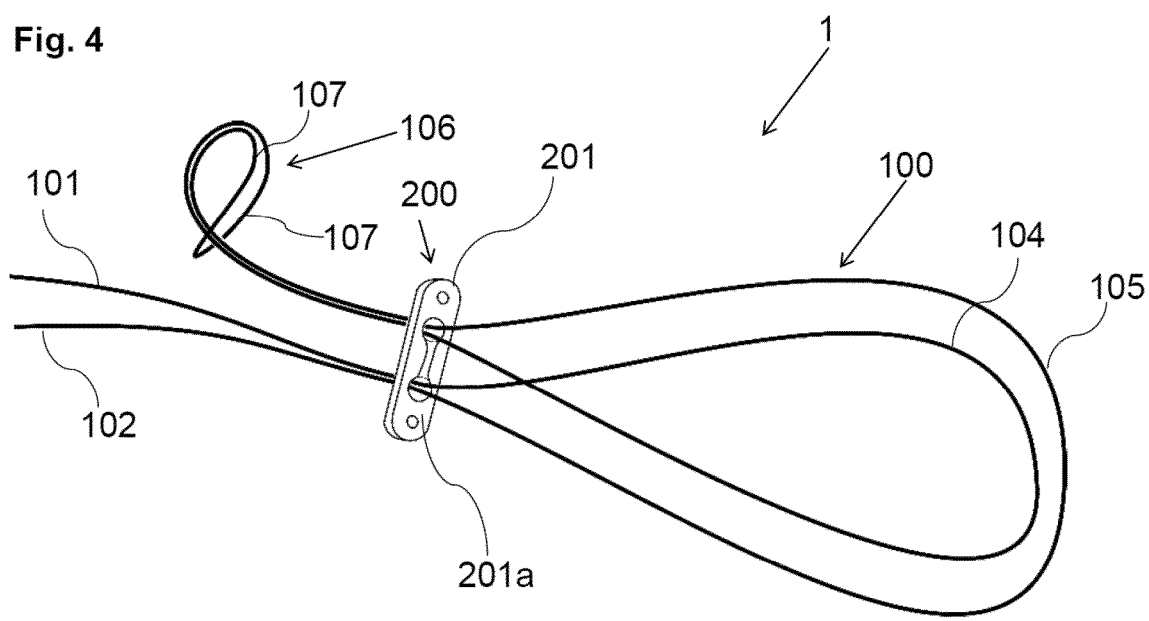
Figure 5:
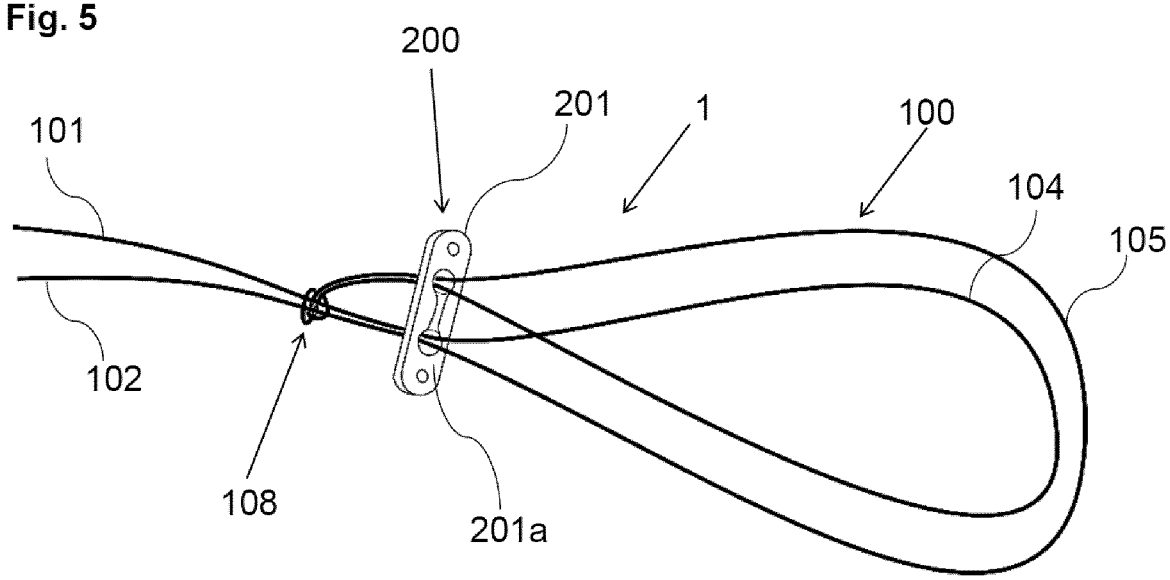
Figure 6:
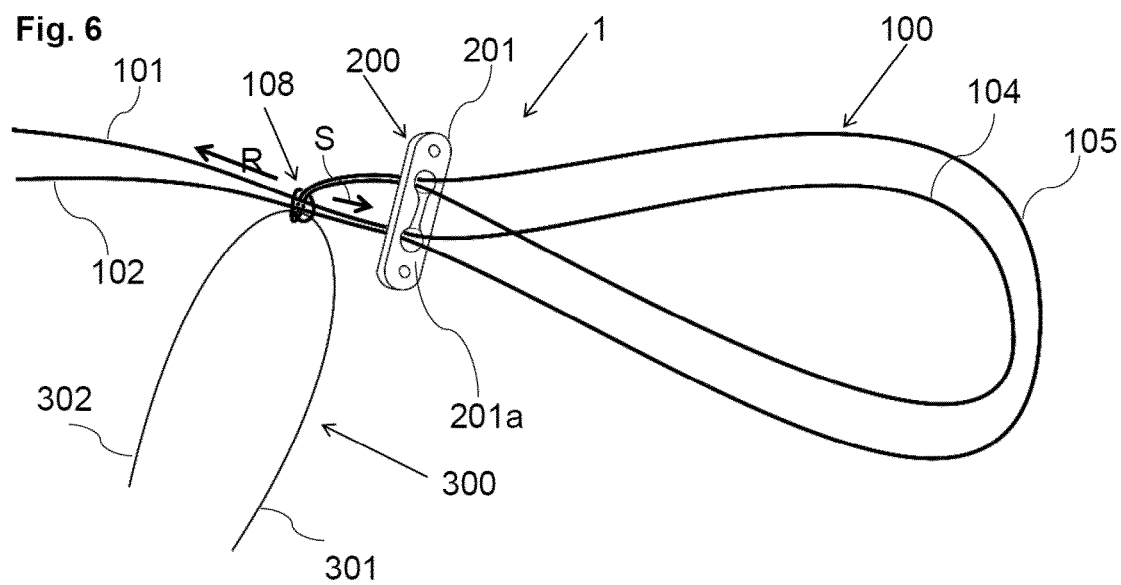
Figure 7:
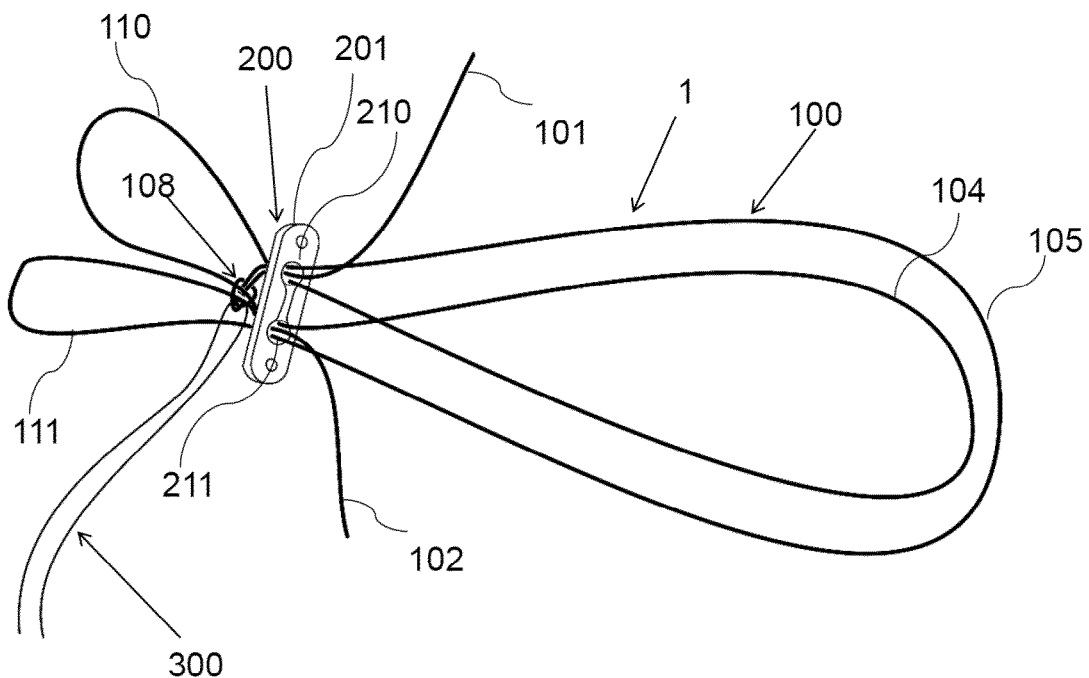
Figure 8:
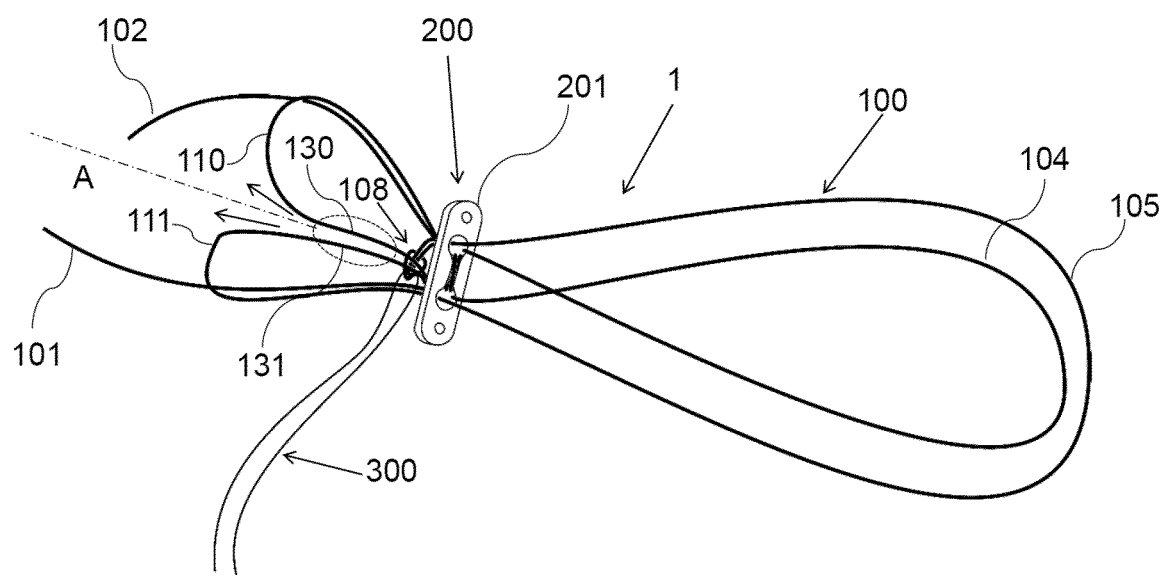
Figure 9:
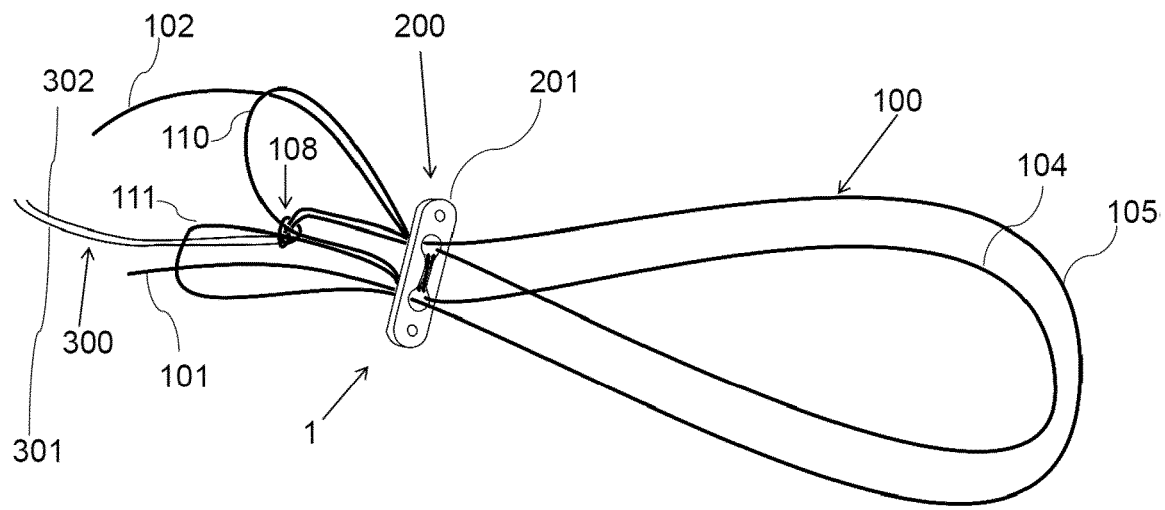
Figure 10:
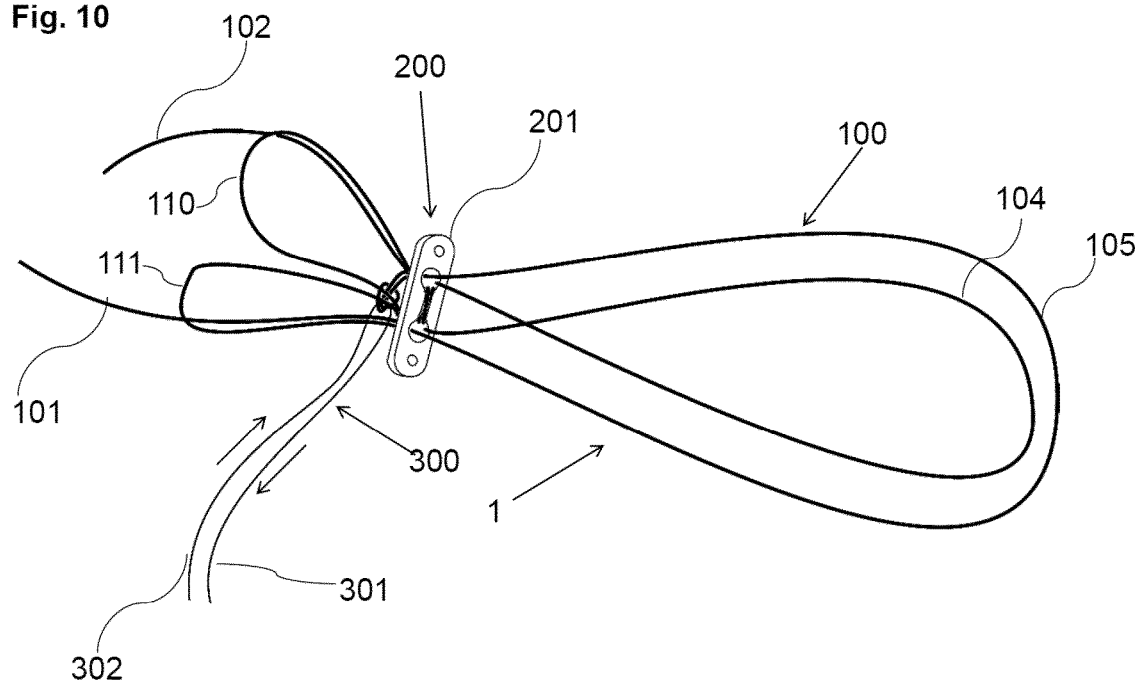
Figure 11:
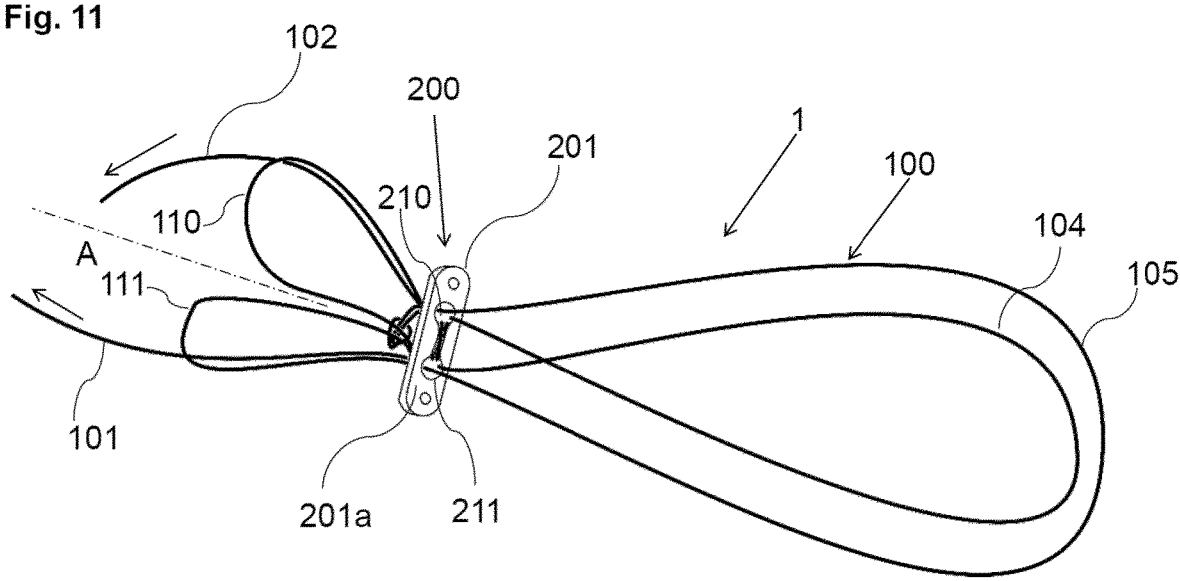
Figure 12:
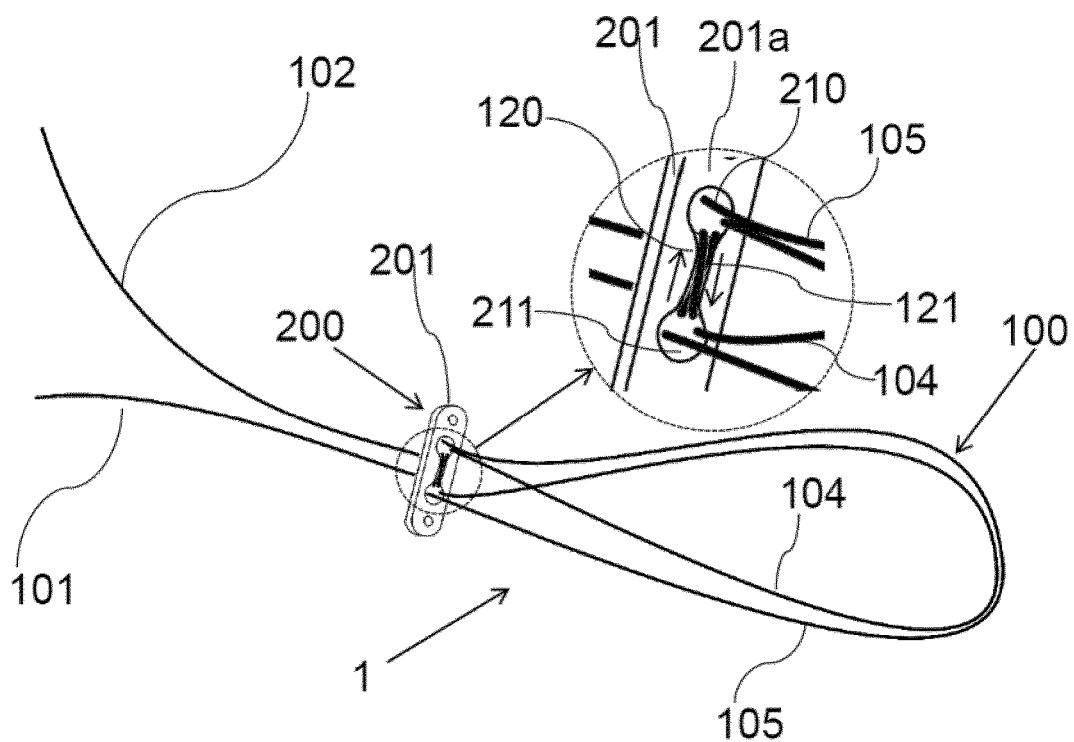

Further features and advantages of the invention shall be described by means of detailed descriptions of embodiments with reference to the Figures, wherein FIG. 1 shows a cortical fixation device (CFD) according to the invention, FIG. 2 shows a medical implant according to the invention comprising a first CFD of FIG. 1 and a first suture thread pulled through the inner through-holes of the first CFD, FIG. 3 shows the medical implant of FIG. 2 comprising a twisted and a non-twisted loop, FIG. 4 shows the medical implant of FIG. 3, wherein the turning loop is formed into a Lark's head, FIG. 5 shows the medical implant of FIG. 4, wherein the Lark's head forms a sliding knot together with the free ends of the first suture thread, FIG. 6 shows the medical implant of FIG. 5, wherein here a second suture thread extends through the loops of the Lark's head, FIG. 7 shows the medical implant of FIG. 6, wherein the free ends of the first suture thread are pulled through the inner through-holes for forming a first and a second loop on the rear side of the first CFD, FIG. 8 shows the medical implant of FIG. 7, wherein the free ends of the first suture thread are further pulled through the respective other inner through-hole, wherein the size of the twisted and the non-twisted loop on the front side of the first CFD can be adjusted by pulling sections of the first and second loop on the rear side of the first CFD, FIG. 9 shows the medical implant of FIG. 8, wherein the sliding knot is moved away from the rear side of the first CFD to loosen and particularly prolong the twisted and the non-twisted loop, FIG. 10 shows the medical implant, wherein the second suture thread is removed, FIG. 11 shows the medical implant of FIG. 10, wherein the first suture thread is secured by means of a slot of the first CFD, FIG. 12 shows the medical implant of FIG. 11 with tightened sliding knot, the zoomed part shows two portions of the first suture thread that are embedded within the slot on the front side of the first CFD.

Figure 13:
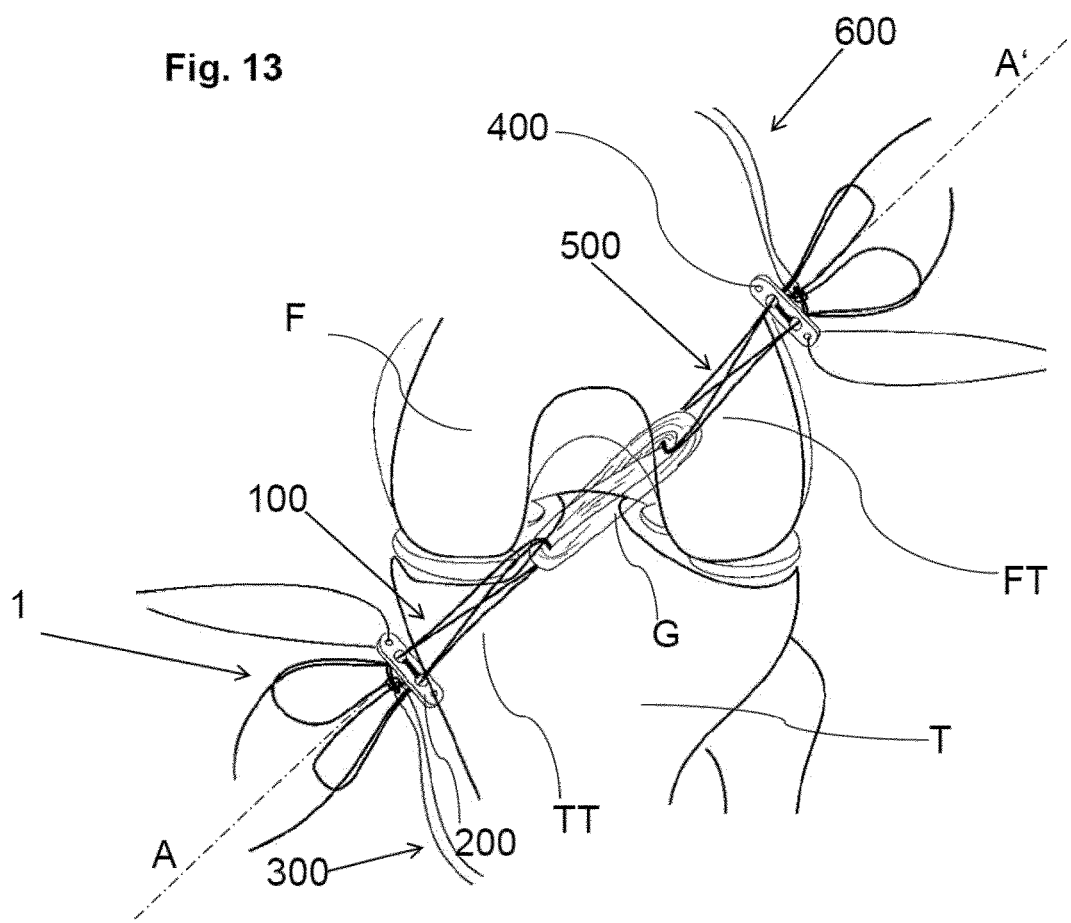
Figure 14:
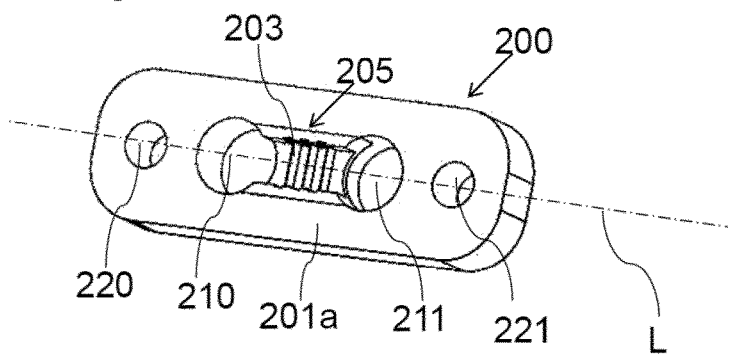
Figure 15:
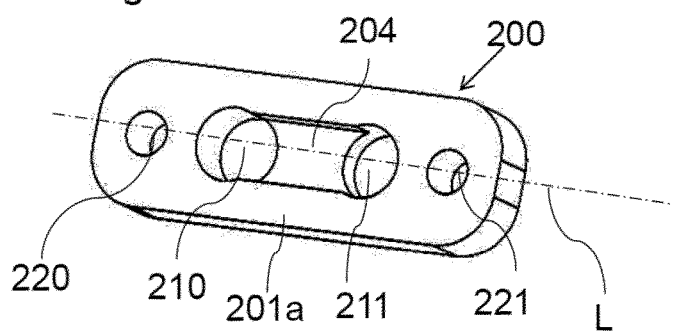
Figure 16:
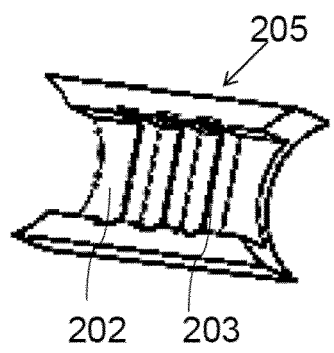

FIG. 13 shows an embodiment of the medical implant having two CFDs for fixing a graft/member that is connected to the CFDs via a first and a third suture thread, and FIGS. 14-16 show an embodiment of a CFD according to the invention.

FIG. 1 shows in conjunction with FIGS. 14 to 16 and FIGS. 2 to 12 a medical implant 1 according to the invention which may comprise a graft G (cf. FIG. 13) or some other flexible (e.g. elongated) member for replacing a defect ligament or tendon, particularly an ACL, which can be connected to a twisted loop 104 and an non-twisted loop 105 formed by a first suture thread 100 of the implant 1.

The implant 1 comprises a first cortical fixation device (CFD) 200 which comprises four through-holes 210, 211, 220, 221, namely two inner through-holes 210, 211 and two optional outer through-holes 220, 221 having an inner diameter that is particularly smaller than the diameters of the inner through-holes 210, 211.

According to FIG. 1 said first cortical fixation device 200 comprises an e.g. elongate body 201 having a front side 201*a* and a rear side 201*b*, which rear side 201*b* faces away from the front side 201*a*. The front side 201*a* is configured to make contact with a bone (e.g. tibia or femur) in order to suspend the graft G (cf. FIG. 13) from the respective bone.

The through holes 210, 211, 220, 221 extend from said front side 201a to the rear side 201b of said body 201 of the first CFD 200.

Furthermore, the first side 201a comprises a slot 202 for receiving a first suture 100 thread 100 of the implant 1, which slot 202 extends on the first side 201a from the first through-hole 210 to the second through-hole 211. For fixing the first suture thread 100, the slot 202 preferably comprises a structure for enhancing friction, particularly plurality of teeth 203, which may extend perpendicular to the longitudinal axis L.

Particularly, as shown in FIGS. 14 to 16, the first side 201a of the body 201 may comprise a recess 204 (cf. FIG. 15), wherein an insert 205 (cf. FIG. 16) is arranged in the recess 204, which insert 205 forms said slot 202 for receiving the first suture thread 100, which slot comprises said teeth 203.

Particularly, in order to configure the implant 1 according to the invention, a first and a second free end of the first suture thread 100 are e.g. guided through the first inner through-hole 210 starting on the rear side 201b of the body 201. Then the two free ends 101, 102 are inserted into the other (second) inner through-hole 211 from the front side 201a and are pulled through, to establish the configuration shown in FIG. 2, which in detail comprises a twisted and a non-twisted loop 104, 105 (cf. FIG. 3) on the first side 201a of the first CFD 200 and a turning loop 103 and the two free ends 101, 102 of the first suture thread 100 on the rear side 201b of the body 201.

As shown in FIG. 4, the implant 1 further comprises a sliding knot 108 formed out of a Lark's head 106 that comprises two adjacent loops 107 through which the two free ends 101, 102 are pulled to form the knot 108.

For this, one may fold the turning loop 103 of the first suture thread 100 upwards in FIG. 3 and place it on top of the still aligned sections of the first suture thread 100 to achieve the configuration shown in FIG. 4, which comprises the two adjacent (e.g. raindrop-shaped) loops 107. Pulling the two free suture thread ends 101, 102 through the adjacent loops 107 yields a self-tightening sliding knot 108.

In order to add a loosening structure, i.e. a means to move/loosen the sliding knot 108, the implant 1 preferably comprises a second suture thread 300 which is inserted into the loops 107 of the sliding knot 108 as shown in FIG. 6.

The second suture thread 300 allows to pull the sliding knot 108, loosen the knot 108, and to elongate the twisted and non-twisted loop 104, 105 in order to adjust the loop length of the device 1. Thus, advantageously, the implant 1 according to the invention comprises a retightenable twisted and non-twisted loop 104, 105.

Particularly, in an embodiment, the sliding knot 108 is configured to slide in a direction S pointing towards the rear side 201b of the cortical fixation device 200 for tightening said twisted loop 104 and said non-twisted loop 105 against motion in the reverse direction R, wherein preferably the second suture thread 300 is configured to bring the sliding knot 108 away from the cortical fixation device 200 so as to loosen the twisted and the non-twisted loop 104, 105 and permit motion in the reverse direction R as indicated in FIG. 6.

Further, as shown in FIG. 7, the first free end 101 of the first suture thread 100 is inserted into the first inner through-hole 210 and the second free end 102 of said first suture thread 100 is inserted into the second inner through-hole 211 in order to create a first and a second loop 110, 11 of the first suture thread 100 on the rear side 201b of the body 201.

Then, the respective free end 101, 102 is pulled back through the respective other inner through-hole 211, 210 on the front side 201a of the body 201 of the first CFD 200, so that portions 120, 121 of the first suture thread lie on top of the structure/teeth 203 within the slot 202 of the first CFD 200 which is shown in FIG. 8 (cf. FIG. 12 for details).

Advantageously, said first and second loop 110, 111 enable a knot-free fixation by e.g. axial pulling.

To make the loop length of the twisted and the non-twisted loop 104, 105 shorter, the aligned sections 130, 131 of the first suture thread 100 extending from the sliding knot 108 can be pulled away (e.g. along axis A) from the rear side 201b of the body 201 as indicated in FIG. 8. It is possible to alternate pulling on each section 130, 131 incrementally.

In case an over-pulling situation happens, the surgeon can loosen the twisted and non-twisted loop 104, 105 by taking both free ends 301, 302 of the second suture thread 300 and by pulling them away from the rear side 201b of the body 201. The loosening effect elongates the loop length of the whole device 1, as shown in FIG. 9.

Once the desired length of the twisted and the non-twisted loop 104, 105 is achieved, the loop can be re-tightened again be repeating the step in FIG. 8. Then, the second suture thread 300 can be pulled out and discarded, e.g. by pulling on only one free end 301, 302, e.g. on free end 301 as indicated in FIG. 10.

In order to finally tighten the first and second loop 110, 111, both free ends 101, 102 can be taken and pulled in a direction away from the rear side 201b of the body 201 of the first CFD 200 as indicated in FIG. 11 (e.g. along axis A). In a clinical setting the direction in which the free ends 101, 102 of the first suture thread 100 need to be pulled could be e.g. in the axial direction A' of the femoral tunnel FT (cf. e.g. FIG. 13).

Finally, the first suture thread 100 is secured by pulling (knot-free), wherein the securing effect stems from the friction at the portions 120, 121 that are embedded in the slot 202 comprising said structure/teeth 203 as shown in the detail of FIG. 12, and particularly the course of the first and second loop 110, 111. The secured implant 1 is shown in FIG. 12. For additional security, several half hitches in opposite directions with the free ends 101, 102 of the first suture thread 100 can be applied as an option.

The CFD 200 according to the invention is preferably used within the framework of the present invention. However, the configuration of the suture threads 100, 300 can also be combined with standard buttons/endobuttons, or any other compatible CFDs.

The implant 1 according to the invention can particularly be used for human or veterinary soft tissue such as tendon/ligament/synthetic graft fixation/repair/reconstruction on one side, or on both sides.

In this regard, FIG. 13 shows an example of a hamstring graft G that is held on both sides, namely by a first CFD 200 and a second CFD 400 that can be designed like the first CFD 200.

Particularly, here, the first suture thread 100 extends in a tibial tunnel TT that extends along axis A while a third suture thread 500 that may be configured as the first suture thread 100 (see FIG. 13) extends through a femoral tunnel FT along axis A'. Here, the first side 201a of the body 201 of the first CFD 200 butts against the tibia T, while the first side (with slot) of the body of the second CFT 400 butts against the femur F, so that the graft G is suspended from the CFTs 200, 400 via the first and third suture threads 100, 500.

The CFD 200, 400 according to the invention can be made of an (particularly biocompatible) metal such as titanium alloy, stainless steel, cobalt-chrome alloy, nickel-titanium alloy, etc. Or a preferably high strength biocompatible polymer, such as polyether ether ketone (PEEK), ultra-high-molecular-weight polyethylene (UHMWPE), poly(tetrafluoroethylene), etc., or a combination of both. FIGS. 14 to 16 show a hybrid design of the CFD 200, 400 already described above, wherein the body 201 can be made of a metal, while said insert 205 that may be connected to the body 201 e.g. by means of a force-fit connection can be made of a polymer. This design reduces the production barrier of a slot 202 with teeth 203 and allows to optimize/choose the slot size in order to fit/adapt with different suture threads 100, 500.

The invention claimed is:

1. A medical implant (1), comprising
at least a first cortical fixation device (200) for fixing a ligament or tendon graft (G) in a desired position, wherein the at least first cortical fixation device (200) comprises a body (201) having a front side (201*a*) and a rear side (201*b*), which rear side (201*b*) faces away from the front side (201*a*), and wherein the body (201) comprises a first and an adjacent second through-hole (210, 211), which through-holes (210, 211) extend from the front side (201*a*) to the rear side (201*b*) of the body, wherein
the medical implant (1) further comprises a first suture thread (100) extending through the through-holes (210, 211) and comprising a twisted loop (104) and a non-twisted loop (105) on the front side (201*a*) of the body (201), and a sliding knot (108) on the rear side (201*b*) of the body (201), and wherein the medical implant (1) comprises a second suture thread (300) extending through the sliding knot (108), and wherein the second suture thread (300) is configured to bring the sliding knot (108) away from the cortical fixation device (200) so as to loosen the twisted and non-twisted loop (104, 105), wherein the front side (201*a*) of the body (201) comprises a slot (202) that accommodates the first suture thread (100), wherein the slot (202) extends from the first through-hole (210) to the second through-hole (211), and wherein the slot provides a knot-free fixation of the first suture thread (100) in the slot (202) by clamping two portions (120, 121) of the first suture thread (100) accommodated side by side in the slot (202).

2. The medical implant according to claim 1, wherein the sliding knot (108) is configured to slide in a direction (S) pointing towards the rear side (201*b*) of the at least first cortical fixation device (200) for tightening the twisted loop (104) and the non-twisted loop (105).

3. The medical implant according to claim 1, wherein the first suture thread (100) comprises a first and a second free end (101, 102), wherein the free ends (101, 102) are threaded through the two through-holes (101, 102) such that the first suture thread (100) forms the twisted loop (104) and the non-twisted loop (105) on the front side (201*a*) of the body (201).

4. The medical implant according to claim 3, wherein the first suture thread (100) comprises a sliding knot (108) on the rear side (201*b*) of the body (201), the sliding knot (108) comprising a Lark's head (106) which comprises two adjacent loops (107) through which the free ends (101, 102) extend.

5. The medical implant according to claim 4, wherein the second suture thread (300) extends through the two adjacent loops (107) of the Lark's head (106) such that the second suture thread (300) forms a loop.

6. The medical implant according to claim 3, wherein the first free end (101) of the first suture thread (100) is passed through the first through-hole (210) so that the first suture thread (100) comprises a first loop (110) on the rear side (201*b*) of the body (201), and wherein the second free end (102) of the first suture thread (100) is passed through the second through-hole (211) so that the first suture thread (100) comprises a second loop (111) on the rear side (201*b*) of the body (201).

7. The medical implant according to claim 6, wherein the first free end (101) further extends through the second through-hole (211) so that a first portion (120) of the first suture thread (100) is embedded in the slot (202), wherein the second free end (102) further extends through the first through-hole (210) so that a second portion (121) of the first suture thread (100) is embedded in the slot (202) so that the two portions (120, 121) extend along each other from opposite directions and are clamped in the slot (202).

8. The medical implant according to claim 7, wherein for securing the twisted and the non-twisted loop (104, 105), the free ends (101, 102) of the first suture thread (100) are configured to be pulled away from the rear side (201*b*) such that the first and the second loop (110, 111) on the rear side (201*b*) are tightened while the twisted and the non-twisted loop (104, 105) are secured with help of the two portions (120, 121) being arranged in the slot (202).

9. The medical implant according to claim 6, wherein for shortening a length of the twisted loop (104) as well as a length of the non-twisted loop (105), the first and the second loop (110, 111) each comprise a section (130, 131) extending from the sliding knot (108), such that, when these sections (130, 131) are pulled away from the rear side (201*b*) the lengths decrease.

10. The medical implant according to claim 1, wherein the front side (201*a*) comprises a recess (204), wherein an insert (205) is arranged in the recess (204), which insert (205) forms the slot (202) for receiving the first suture thread (100).

11. The medical implant according to claim 1 wherein the slot (202) comprises a structure (203) comprising a plurality of teeth (203) for securing the first suture thread (100).

12. The medical implant according to claim 10, wherein the insert (205) is formed out of a synthetic material, such as polyether ether ketone, polyethylene, ultra-high-molecular-weight polyethylene (UHMWPE), poly(propylene), poly (tetrafluoroethylene), poly(methyl methacrylate), ethylene-co-vinylacetate, poly(ether urethane), poly(ethylene terephthalate).

13. The medical implant according to claim 1, wherein for increasing a length of the twisted loop (104) and a length of the non-twisted loop (105), a first and a second free end (301, 302) of the second suture thread (300) are configured to be pulled away from the rear side (201*b*) in order to pull the sliding knot (108) away from the rear side (201*b*) such that the- lengths are increased.

14. The medical implant according to claim 1, wherein the body (201) is formed as an elongated plate that extends along a longitudinal axis (L), wherein the through-holes (210, 211) are arranged side by side in the direction of the longitudinal axis (L).

15. The medical implant according to claim 1, wherein the two through-holes (210, 220) are inner through holes (210, 211), wherein the body (201) comprises two outer through-holes (220, 221), wherein each outer through-hole (220, 221) extends from the front side (201*a*) to the rear side (201*b*), and wherein the outer through-holes (220, 221) face each other in the direction of a longitudinal axis (L), wherein the two inner through-holes (210, 211) are arranged between the two outer through-holes (220, 221).

16. The medical implant according to claim 15, wherein the inner diameter of the inner through-holes (210, 211) is larger than the inner diameter of the outer through-holes (220, 221).

17. The medical implant according to claim 1, wherein the body (201) is formed out of a metal and/or a synthetic material, wherein the metal is one of: titanium alloy, stainless steel, cobalt-chrome alloy, nickel-titanium alloy, and wherein the synthetic material is one of: biocompatible synthetic material, particularly a high strength biocompatible synthetic material, polyether ether ketone, ultra-high-molecular-weight polyethylene (UHMWPE), poly(tetrafluoroethylene).

18. The medical implant according to claim 1, wherein the twisted loop (104) and the non-twisted loop (105) are configured to be connected to the tendon or ligament graft (G) so that the tendon or ligament graft (G) which extends through the twisted and non-twisted loop (104, 105).

19. A cortical fixation device (200) for fixing a ligament or tendon graft (G) in a desired position, comprising a body (201) having a front side (201*a*) and a rear side (201*b*), which rear side (201*b*) faces away from the front side (201*a*), and wherein the body (201) comprises a first and an adjacent second through-hole (210, 211), which through-holes (210, 211) extend from the front side (201*a*) to the rear side (201*b*) of the body (201), wherein
the front side (201a) of the body (201) comprises a slot (202) accommodating a suture thread (100) thereby providing a knot-free fixation of the suture thread (100) in the slot (202), wherein the slot (202) extends from the first through-hole (210) to the second through-hole (211), and wherein the slot (202) comprises a plurality of teeth securing the suture thread (100) in the slot (202) by way of friction between the teeth and the suture thread.

20. The cortical fixation device according to claim 19, wherein the front side (201*a*) comprises a recess (204), wherein an insert (205) is arranged in the recess (204), which insert (205) forms the slot (202) for receiving the suture thread (100).

21. The cortical fixation device according to claim 20, wherein the insert (205) is formed out of a synthetic material.

22. The cortical fixation device according to claim 19, wherein the structure for enhancing friction is a plurality of teeth (203).

23. The cortical fixation device according to claim 19, wherein the body (201) is formed as an elongated plate that extends along a longitudinal axis (L), wherein the through-holes (210, 211) are arranged side by side in the direction of the longitudinal axis (L).

24. The cortical fixation device according to claim 19, wherein the two through-holes (210, 220) are inner through holes (210, 211), wherein the body (201) comprises two outer through-holes (220, 221), wherein each outer through-hole (220, 221) extends from the front side (201*a*) to the rear side (201*b*), and wherein the outer through-holes (220, 221) face each other in the direction of a longitudinal axis (L), wherein the two inner through-holes (210, 211) are arranged between the two outer through-holes (220, 221).

25. The cortical fixation device according to claim 24, wherein the inner diameter of the inner through-holes (210, 211) is larger than the inner diameter of the outer through-holes (220, 221).

26. The cortical fixation device according to claim 19, wherein the body (201) is formed out of a metal.

27. A method for fixing a ligament or tendon graft (G) in a desired position, wherein the method uses the medical implant according to claim 1, wherein the first suture thread (100) is threaded through the through-holes (210, 211), and formed into the twisted loop (104) and thea non-twisted loop (105) being arranged on the first side (201*a*) of the body (201), wherein the twisted and the non-twisted loop (104, 105) are looped around a section of the ligament or tendon graft (G) to hold the latter and fix it to the bone, and wherein the first suture thread is tied to form thea sliding knot (108) on the rear side (201*b*) of the body (201), and wherein thea second suture thread (300) is threaded through the sliding knot (108) to allow loosening of the sliding knot (108), and wherein the two portions (120, 121) of the first suture thread (100) are clamped within thea slot (202) of the body (201) for providing the knot-free fixation of the first suture thread (100) in the slot (202).

* * * * *